United States Patent
Minton

(10) Patent No.: US 6,969,606 B2
(45) Date of Patent: Nov. 29, 2005

(54) LOCKABLE CONTACT PLATE

(75) Inventor: Kenneth Minton, West Linn, OR (US)

(73) Assignee: PML Microbiologicals, Inc., Wilsonville, OR (US)

( * ) Notice: Subject to any disclaimer, the term of this patent is extended or adjusted under 35 U.S.C. 154(b) by 0 days.

(21) Appl. No.: 10/695,066

(22) Filed: Oct. 27, 2003

(65) Prior Publication Data

US 2005/0089996 A1 Apr. 28, 2005

(51) Int. Cl.[7] ............................................... C12M 1/34
(52) U.S. Cl. ........................... 435/288.3; 435/305.3; 435/305.4; 422/102
(58) Field of Search ................. 422/102; 435/288.3, 435/305.3, 305.4

(56) References Cited

U.S. PATENT DOCUMENTS

| | | | |
|---|---|---|---|
| 3,769,936 A | 11/1973 | Swanson et al. | |
| 4,634,676 A | * 1/1987 | Sapatino | 435/309.4 |
| 5,021,351 A | 6/1991 | Ervin | |
| 5,282,874 A | 2/1994 | Tsukagoshi | |
| 5,292,026 A | 3/1994 | Stolzman | |
| 5,520,302 A | 5/1996 | Anderson et al. | |
| 5,638,976 A | * 6/1997 | Arnold | 220/298 |
| 5,657,895 A | 8/1997 | Rogge | |
| 5,695,988 A | * 12/1997 | Chong | 435/305.1 |
| 5,725,123 A | 3/1998 | Otto-Nagels | |
| 5,854,065 A | 12/1998 | Livingston et al. | |
| 6,602,704 B1 | * 8/2003 | Maxwell et al. | 435/305.4 |

* cited by examiner

Primary Examiner—David A. Redding
(74) Attorney, Agent, or Firm—Chernoff, Vilhauer, McClung & Stenzel, LLP

(57) ABSTRACT

A lockable contact plate is disclosed wherein the lid and base of the dish are provided with at least two pairs of locking members, each comprising a radial sheath and a sheath-engaging tab.

9 Claims, 3 Drawing Sheets

LOCKABLE CONTACT PLATE

BACKGROUND OF THE INVENTION

The use of Petri dishes for growing colonies of microorganisms such as bacteria or fungi is well known. A variation on the concept of a Petri dish has developed in recent years, namely, a so-called "contact plate." A contact plate is a much smaller version of a Petri dish, the dish component of which is provided with a base for grasping the contact plate, and a cover. Contact plates are typically fabricated from polymeric material in mass quantities at a sufficiently low cost as to be disposable after a single use. In use, the convex bottom of the contact plate is filled with microorganism growth medium such as agar, resulting in a convex mound of growth medium. With the lid removed, the contact plate is grasped by the base and the mound of growth medium is pressed against a surface to be tested for bacterial and/or fungal contamination. The lid is then replaced and the contact plate is stored in an environment conducive to microorganism growth. A typical contact plate is pre-loaded with growth medium under sterile conditions and packaged for shipment to the end user.

Two known designs of contact plates are those that are the subject of U.S. Pat. Nos. 5,854,065 and 6,602,704. Both designs have the inherent drawback that the lid and base are held together by a compression fit that is often either too tight to allow ready disengagement between the lid and base or too loose, which can lead to accidental spillage or contamination when handling the contact plate.

What is needed therefore is a lockable contact plate that does not lock except upon application of a specific intentionally applied force, that provides a secure locking engagement between the lid and the base, and which may be readily disengaged from the locking engagement. These needs are met by the present invention, which is summarized and described in detail below.

BRIEF SUMMARY OF THE INVENTION

The present invention comprises a lockable contact plate wherein the lid and base components of the contact plate are prevented from premature or accidental locking engagement with each other so as to permit rapid pre-loading with growth medium, yet are readily lockable and unlockable from each other.

DETAILED DESCRIPTION OF PREFERRED EMBODIMENTS

Figure 1:
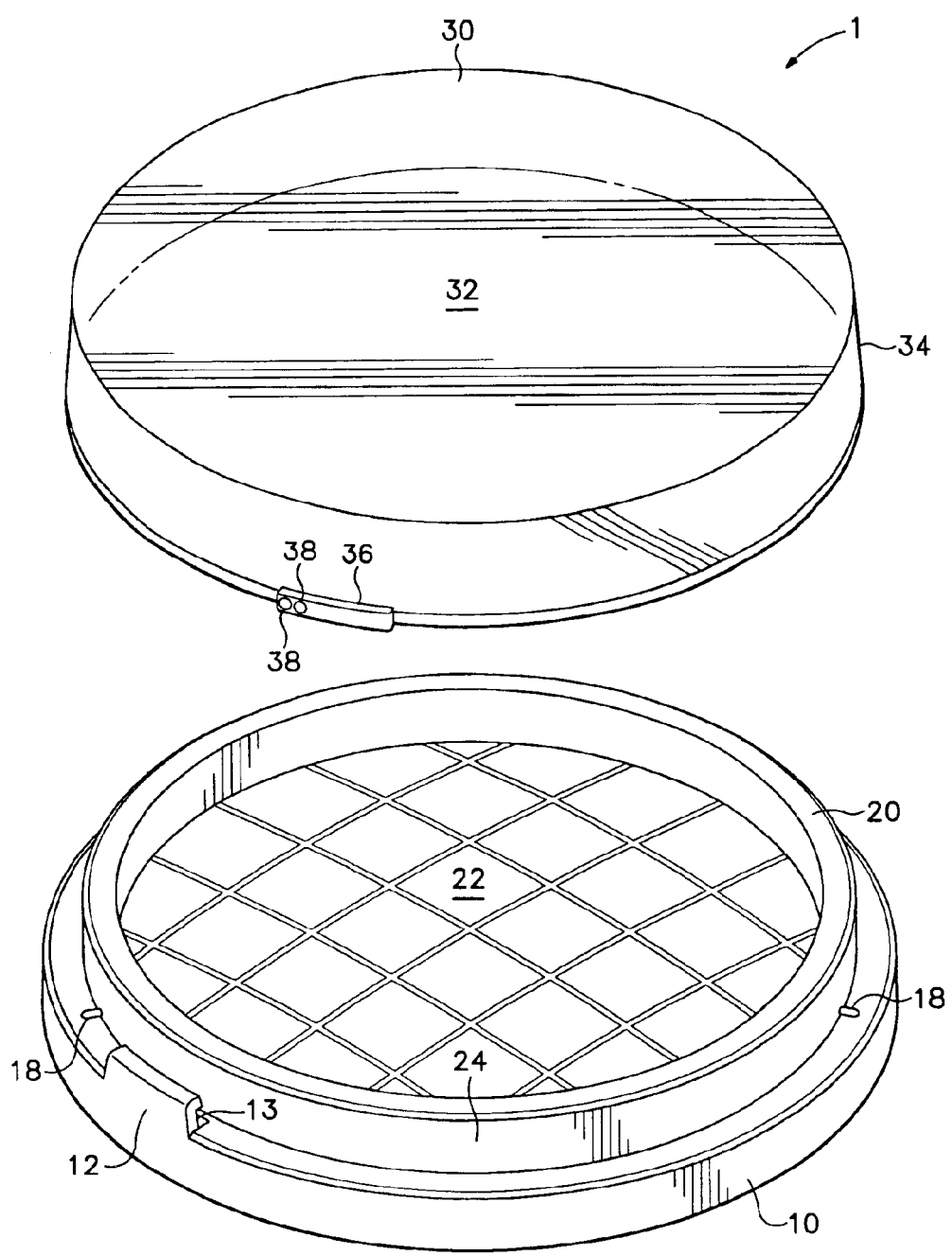
FIG. 1 is an exploded perspective view of an exemplary embodiment of the contact plate of the invention.
Figure 2:
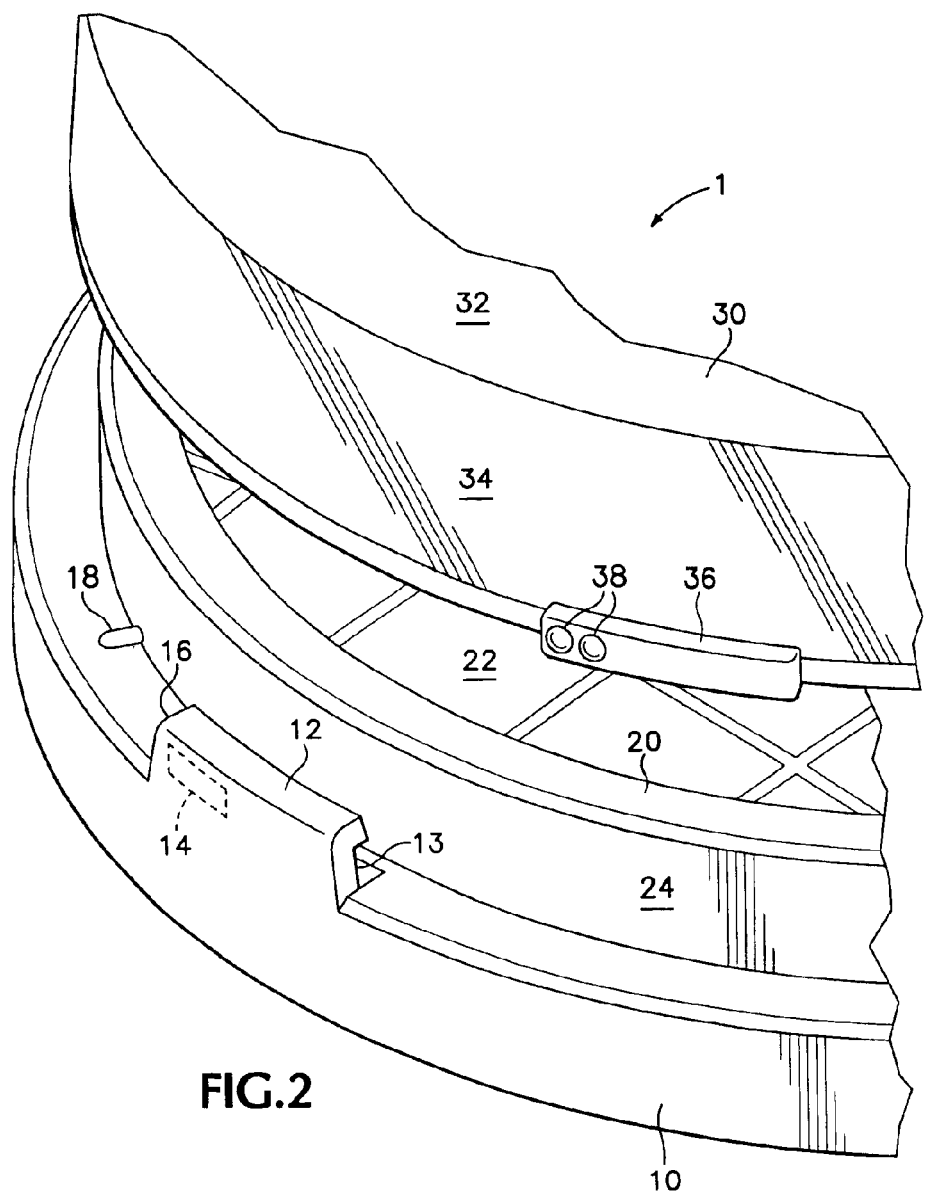
FIG. 2 is a close-up view of FIG. 1.
Figure 3:
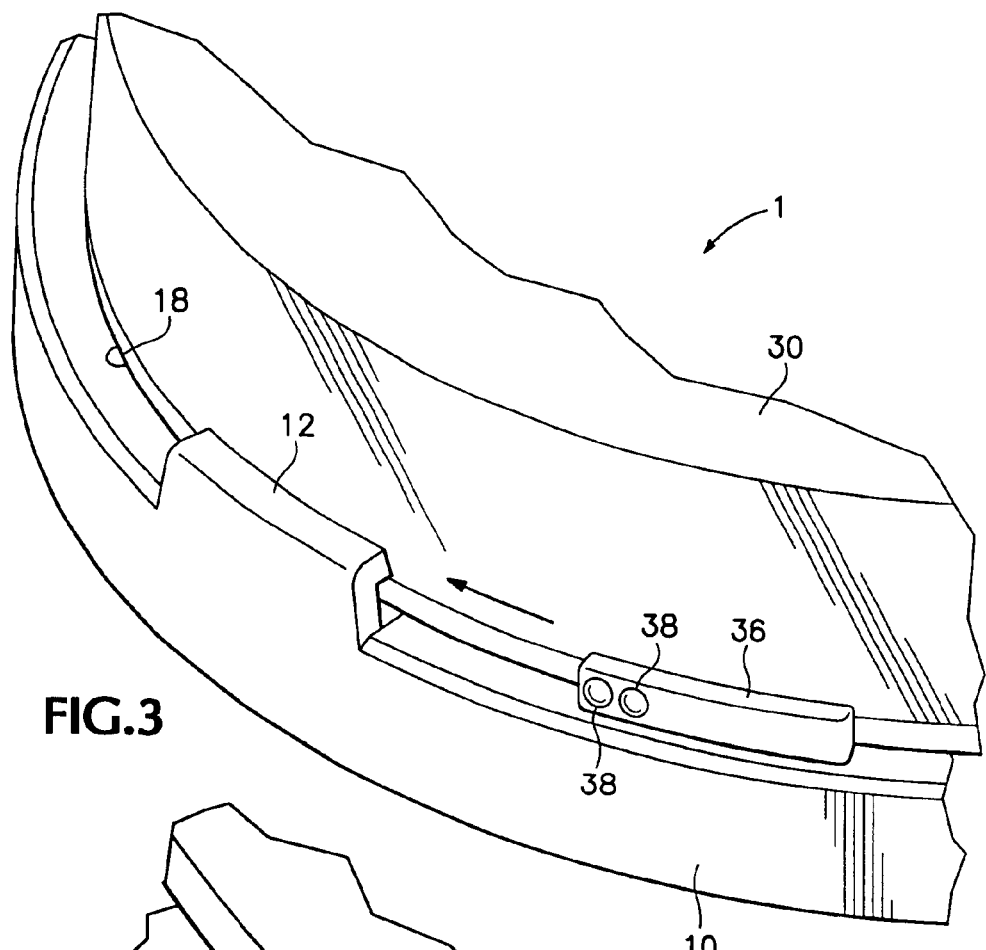
FIG. 3 is a partial perspective view of FIG. 1 showing alignment of exemplary locking elements of the invention.
Figure 4:
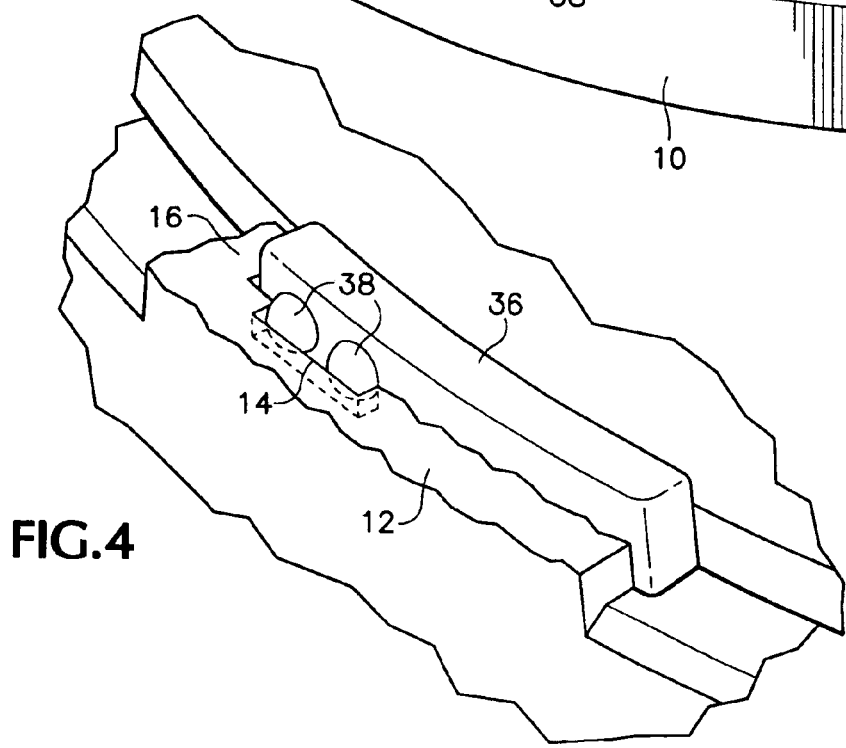
FIG. 4 is a partial perspective view of FIG. 3 with a cutaway view of one of the locking elements.

Referring to the drawings, wherein the same numerals refer to like elements, there is shown in FIGS. 1–4 a contact plate 1 comprising a circular dish 20 supported on a circular base 10, dish 20 consisting of a convex bottom plate 22 and a bottom cylindrical sidewall 24. Bottom plate 22 of dish 20 preferably has a grid superimposed thereon, shown in FIGS. 1–2, for purposes of accurately recording microorganism growth by quadrant. Most growth media is at least translucent, so that when the contact plate is filled with a growth medium, the grid is visible through the medium. The contact plate further comprises a circular lid 30, consisting of a lid top plate 32 and a top cylindrical side wall 34. Lid 30 is preferably transparent so as to permit viewing of any microorganism growth.

Base 10 and lid 30 are provided with locking means for securing the base and lid in locking engagement. The locking means comprises at least two pairs of locking members radially spaced apart from each other, preferably equidistantly, wherein each pair of locking members comprises sheath and tab members adapted to slidably engage with each other. More specifically, radial sheath 12 is preferably integral with base 10 and has a sheath entry 13; the external radius of radial sheath 12 preferably corresponds to the external radius of base 10. Top cylindrical side wall 34 of lid 30 is provided with an elongate radial tab 36 that is preferably integral with side wall 34, and is sized and shaped so as to be slidably engagable with sheath 12; the external radius of tab 36 preferably is slightly less than that of the external radius of base 10. Although sheath 12 and tab 36 are preferred to be integral with base 10 and lid 30, respectively, it should be understood that this arrangement could be reversed and still yield the desired locking means of the invention.

As mentioned above, it is often advantageous to pre-load dish 20 with a growth medium such as agar or a gel containing microorganism-specific nutrients or indicators, then assemble the base and lid components, seal them in sterile packaging and ship them to the laboratory or other end user. Such pre-loading and prepackaging is typically conducted on an automated basis, assembly-line style, with the lids rapidly being removed and replaced on the bases by a mechanical arm immediately before and after the agar or gel pour. For speed and efficiency, it is best that, immediately before and after the agar or gel loading, the lid not enter into locking engagement with the base as this tends to interfere with and so slow the automated pre-loading process. To prevent premature locking engagement between base 10 and lid 30 on such an assembly line, tab 36 is provided with at least one button-like protrusion 38 that prevents entry of tab 36 into sheath entry 13 absent application of a torquing force. Although protrusion(s) 38 are shown as being generally hemispherical in shape, it should be understood that virtually any shape of protrusion would function as well, including oval and rectangular. When sheath 12 is provided on the inner portion of its outer wall with at least one indent 14 (shown in phantom) sized and shaped so as to fit snugly with protrusion(s) 38 upon application of a torquing force such as would be caused by rotating lid 30 relative to base 10 (schematically shown by the directional arrow in FIG. 3), protrusion(s) 38 also serve to securely lock lid 30 to base 10, thereby permitting the contact plate to be lifted and handled by grasping lid 30 without risk of accidental removal of the lid from the base. Although indent 14 is shown as being generally rectangular in shape in the drawings, it is to be understood that virtually any shape that accommodates protrusion(s) 38 would function as well, including oval and circular.

Preferably tab 36, protrusion(s) 38 and sheath 12 are all fabricated from a polymeric material having a slight degree of resiliency, so that when tab 36 enters sheath 12, those elements both resiliently yield until protrusion(s) 38 are in alignment with indent 14, whereupon they enter into locking engagement. A preferable polymeric material is polysterene.

The same resiliency of sheath 12, tab 36 and protrusion(s) 38 permits lid 30 to be readily disengaged from base 10 by simply rotating the lid in an opposite direction relative to the base. Preferably, to prevent tab 36 from passing all the way through sheath 12, the sheath is provided with an end wall 16 distal to sheath entry 13.

In use, microorganism cell growth may take place on the growth medium of the contact plate either aerobically or anaerobically. In the former case, it is important that the cylindrical sidewall 34 of lid 30 not engage base 10 so tightly as to effectively form a seal against the entry of air, thereby creating a "greenhouse" effect. In the latter case, a space is needed for gas exchange for purposes of displacing air and replacing it with an inert gas such as nitrogen. Accordingly, for both aerobic and anaerobic applications, base 10 is preferably provided with a multiplicity of radially arranged spacers in the form of nubs 18 that create a gap between the cylindrical sidewall 34 of lid 30 and base 10, thereby allowing air to circulate in and through dish 20 or allowing the introduction of inert gas to create an anaerobic environment.

The contact plate of the invention containing growth medium is preferably manufactured in an unlocked arrangement with the leading edge of tab 36 juxtaposed to entry 13 of tab 12, and is packaged for shipment to the end user in gas-impermeable sterile packaging.

The terms and expressions which have been employed in the foregoing specification are used therein as terms of description and not of limitation, and there is no intention in the use of such terms and expressions of excluding equivalents of the features shown and described or portions thereof, it being recognized that the scope of the invention is defined and limited only by the claims which follow.

What is claimed is:

1. A contact plate comprising
   (a) a circular dish supported on a circular base, said dish having a bottom plate and a bottom cylindrical side wall, and
   (b) a circular lid having a top plate and a top cylindrical side wall, said lid sized so as to fit over the bottom cylindrical side wall of said dish
   wherein said base and said lid are provided with locking means for securing said base and said lid in locking engagement, said locking means comprising at least two pairs of locking members, each of said pairs of locking members comprising (i) a radial sheath having an entry, and (ii) an elongate radial tab sized and shaped so as to be slidably engagable with said radial sheath wherein said radial tab has at least one protrusion and said radial sheath has at least one indent, with said protrusion and said indent being sized and located so as matingly engage each other;
   and wherein said at least one protrusion is proximal to the entry of said sheath and said at least one indent is distal to the entry of said sheath;
   and wherein said sheath has a closed end distal to said entry.

2. The contact plate of claim 1 wherein said tab has two protrusions.

3. The contact plate of claim 2 wherein said sheath is integral with said base and said tab is integral with said top cylindrical side wall.

4. The contact plate of claim 3 wherein said sheath and said tab are slidably engagable with each other by rotating said lid relative to said base.

5. The contact plate of claim 4 wherein said sheath and said tab are slidably disengagable from each other by rotating said lid relative to said base.

6. The contact plate of claim 5 wherein said lid is transparent.

7. The contact plate of claim 6 wherein said base has a multiplicity of spacers around its periphery to prevent said lid from sealingly engaging said base.

8. The contact plate of claim 7 wherein said dish contains microorganism growth medium.

9. The contact plate of claim 8 packaged in sterile packaging.

* * * * *

UNITED STATES PATENT AND TRADEMARK OFFICE
CERTIFICATE OF CORRECTION

| | | |
|---|---|---|
| PATENT NO. | : 6,969,606 B2 | Page 1 of 1 |
| APPLICATION NO. | : 10/695066 | |
| DATED | : November 29, 2005 | |
| INVENTOR(S) | : Kenneth Minton | |

It is certified that error appears in the above-identified patent and that said Letters Patent is hereby corrected as shown below:

Column 4, line 10-11: After "as " insert -- to --.

Signed and Sealed this

Twelfth Day of December, 2006

JON W. DUDAS
*Director of the United States Patent and Trademark Office*